United States Patent [19]

Kadaba et al.

[11] Patent Number: 5,942,527

[45] Date of Patent: Aug. 24, 1999

[54] HYDRAZONES, HYDRAZINES, SEMICARBAZONES AND THIOSEMICARBAZONES DERIVED FROM PYRIDYL KETONES AS ANTICONVULSANT DRUGS AND EXCITATORY AMINO ACID ANTAGONISTS

[75] Inventors: Pankaja K. Kadaba, Lexington, Ky.; Zhaiwei Lin, Bethesda, Md.

[73] Assignee: K & K Biosciences, Inc., Lexington, Ky.

[21] Appl. No.: 08/917,925

[22] Filed: Aug. 27, 1997

[51] Int. Cl.[6] .......................... C07D 213/02; A61K 31/44
[52] U.S. Cl. ............................. 514/357; 546/332
[58] Field of Search .............................. 546/332; 514/357

[56] References Cited

U.S. PATENT DOCUMENTS

| | | | |
|---|---|---|---|
| 4,511,572 | 4/1985 | Kadaba | 514/340 |
| 4,610,994 | 9/1986 | Kadaba | 514/340 |
| 4,618,681 | 10/1986 | Kabada | 546/276 |
| 4,683,245 | 7/1987 | Ferrari et al. | 514/652 |
| 4,689,334 | 8/1987 | Kadaba | 514/340 |
| 4,820,721 | 4/1989 | Kadaba | 435/252.1 |
| 4,888,433 | 12/1989 | Giordano et al. | 514/652 |
| 4,933,290 | 6/1990 | Cesti et al. | 435/280 |
| 5,521,158 | 5/1996 | Kyle et al. | 549/450 |
| 5,554,532 | 9/1996 | Matsuyama et al. | 514/16 |

OTHER PUBLICATIONS

Pfenninger et al Chemical Abstracts, vol. 70, No. 16, Abstract 77.795r, p. 331, Apr. 21, 1969.

Wallach et al, Biochim Biophysica Acta, vol. 663, No. 2, pp. 361–372, 1981.

Thummel et al., "Polyaza–Cavity Shaped Molecules. 14. Annelated 2–(2'Pyridyl)indoles, 2,2'–Biindoles, and Related Systems", J. Org. Chem. 1989, 54, pp. 1720–1725.

Watkins et al., "Excitatory Amino Acid Transmitters", Ann. Rev. Pharmacol. Toxicol. 1981, 21, pp. 165–204.

Karabatsos et al., "syn–anti Isomer Determination of 2,4–Dinitrophenylhydrazones and Semicarbazones by N.m.r." JACS, 84, pp. 753–755.

Huntress et al., "Beckmann Rearrangement of the Oximes of Phenyl 2–Pyridyl Ketone (2–Benzoylpyridine)", vol. 70, Nov. 1948, pp. 3702–3707.

Deshmukh et al., "Identification of the Triazoline Pharmacophore and the Evolution of the Aminoalkylpyridines, A New Class of Potent Orally Active Anticonvulsant Agents", Medicinal Chemistry Research, 1993, vol. 3 pp. 223–232.

Kadaba et al., "Triazolines–XXVII.$\Delta_2$–1,2,3–Triazoline Anticonvulsants: Novel 'Build–in' Heterocyclic Prodrugs with a Unique 'Dual Action' Mechanism for Impairing Excitatory Amino Acid L–Glutamate Neurotransmission", Bioorganic & Medicinal Chemistry, vol. 4, No. 2, pp. 165–178, 1996.

A.C. Foster, "Involvement of Excitatory Amino Acid Receptors in the Mechanisms Underlying Excitotoxic Phenomena", 1986, pp. 303–318.

B. Meldrum, "Excitatory Amino Acid Antagonists as Novel Anticonvulsants", 1986, pp. 321–329.

Porter et al., "Antiepileptic Drug Development Program", Cleveland Clinic Quarterly, vol. 51, No. 2, 1984, pp. 293–305.

Porter et al., "Antiepileptic Drug", Basic and Clinical Pharmacology Fourth Edition, 1989, pp. 287–303.

Roger J. Porter, "Mechanisms of Action of New Antiepileptic Drugs", Epilepsia, vol. 30, Suppl. 1, 1989, pp. S29–S34.

Foster et al., "Acidic Amino Acid Binding Sites in Mammalian Neuronal Membranes: Their Characteristics and Relationship to Synaptic Receptors", Brain Research Reviews, vol. 7 (1984) pp. 103–164.

Kolb et al., "Abnormally High IR Frequencies for the Carbonyl Group of Semicarbazones of the Benzaldehyde and Acetophenone Series", J. Org. Chem., 1989, vol. 54, pp. 2341–2346.

Teague et al., "Some Pyridylhydantoins", vol. 75, Jul. 20, 1953, pp. 3429–3430.

Kuhn et al., "Über stereoisomere 2–Acyl–pyridin–phenylhdrazone und die Darstellung von 8–Aza–indazolium–Salzen", Vogel, Jahrg. 85, Nr. 1/1952, pp. 28–37.

Chemical Abstracts, vol. 57, 1962, p. 3420.

(List continued on next page.)

*Primary Examiner*—Zinna Northington Davis
*Attorney, Agent, or Firm*—McDermott, Will & Emery

[57] ABSTRACT

Pharmaceutical compositions comprise as the active ingredient potent orally active, nonneurotoxic anticonvulsant compounds that are highly effective in the MES animal model and are excitatory amino acid antagonists, and that are selected from the groups of hydrazones, hydrazines and semicarbazones consisting of those of the formulae:

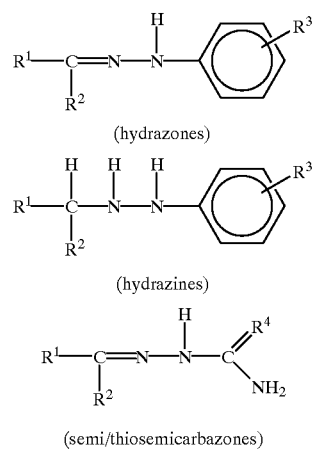

wherein $R^1$ is 4-pyridyl or 3-pyridyl, $R^2$ is methyl, ethyl or phenyl, $R^3$ is 3,4-dichloro, p-chloro or m-chloro and $R^4$ is oxygen. The compositions are administered to mammals in an amount to provide a dosage amount ranging from about 10 mg/kg to 200 mg/kg of body weight.

51 Claims, No Drawings

OTHER PUBLICATIONS

Da Re et al., "Mannich Reaction on 7–Hydroxychromones and Flavones. Synthesis of Powerful Central Nervous System Stimulants", vol. 25, Jul. 1960, pp. 1097–1100.

Stenberg et al., "Nitrogen Photochemistry. syn and anti Isomers of Semicarbazones", The Journal of Organic Chemistry, 1968, vol. 33, No. 12, pp. 4402–4406.

Nelson et al., "Decomposition of Quaternary Ammonium Salts. IV. Methyl Ketones", JACS, vol. 77, 1955, p. 1908.

Chu et al., "4–Pyridylhydantoins", Journal of Organic Chemistry, 1958, vol. 23, p. 1578.

Butler et al., "Stereoisomerization in Heterocyclic Hydrazones Derived from 2–Acylpyridines and their Oxidative Cyclization with Mercury Acetate and Lead Tetra–acetate to Fused 1,2,4–Triazoles and 1,2,3–Triazolium Systems", J. Chem. So. Perkin Trans. 1, 1984, pp. 2109–2116.

Davison et al., "Infrared Spectra of Semicarbazones", 1955, pp. 3389–3391.

Felder et al., "Rissunto", Piridinaldeidi, 1955, pp. 386–391.

Frank D. Popp, "Potential Anticonvulsants. IX. Some Isatin Hydrazones and Related Compounds", J. Heterocyclic Chem., vol. 21, Nov.–Dec. 1984, pp. 1641–1645.

Frank D. Popp, "Potential Anticonvulsants. VIII. Some Hydrazones of Indole–3–carboxaldehyde", J. Heterocyclic Chem., vol. 21, Mar.–Apr. 1984, pp. 617–619.

Lukevics et al., "Neurotropic activity of aldehyde and ketone thiosemicarbazones with a heterocyclic component", Eur. J. Med. Chem. (1995) vol. 30, pp. 983–988.

Chemical Abstracts, vol. 112, 1990.

Frank D. Popp, "Potential anticonvulsant. XII. Anticonvulsant activity of some aldehyde derivative", Eur. J. Med. Chem., vol. 24, 1989, pp. 313–316.

HYDRAZONES, HYDRAZINES, SEMICARBAZONES AND THIOSEMICARBAZONES DERIVED FROM PYRIDYL KETONES AS ANTICONVULSANT DRUGS AND EXCITATORY AMINO ACID ANTAGONISTS

FIELD OF THE INVENTION

This invention relates to novel anticonvulsant hydrazones, hydrazines, semicarbazones and thiosemicarbazones derived from pyridyl ketones and their method of preparation, and more particularly relates to novel anticonvulsant hydrazones, hydrazines, semicarbazones and thiosemicarbazones derived from pyridyl ketones which are useful as excitatory amino acid inhibitors and potent orally active antiepileptic pharmaceutical compositions with no neurotoxicity.

BACKGROUND ART

Epilepsy is a leading neurological disorder, second only to stroke. One to four million Americans and twenty to forty million people world-wide suffer from some form of epilepsy, making it second only to stroke as the leading neurological disorder. Although standard therapy permits control of seizures in 80% of these patients, one-half million people in the U.S. have uncontrolled epilepsy. The number of drugs useful for the treatment of epilepsy is remarkably small. Fewer than 20 drugs are currently marketed in the U.S., and of these, only five or six are widely used. Complex partial epilepsy (also known as temporal lobe, psychomotor or limbic epilepsy), the most devastating form among adults, and estimated to account for as many as two-thirds of all cases, is refractory to drug treatment [Gummit, R. J., "The Epilepsy Handbook, The Practical Management of Seizures", Raven Press, New York, 1983]. It is becoming increasingly evident that significant progress toward complete control can be achieved only by an understanding of the mechanisms of the epilepsies themselves, which will provide the molecular basis for antiepileptic drug design and development, and new treatment strategies.

NMDA (N-methyl-D-aspartate) receptor overstimulation by high levels of the excitatory amino acid (EAA), L-glutamate, has been implicated in epileptogenesis and epilepsy [Cavalheiro, et al., "Frontiers in Excitatory Amino Acid Research", A. R. Liss, New York, 1988]. Thus, development of agents that are EAA/NMDA antagonists may constitute novel and effective therapies for the epilepsies. Although a number of EAA inhibitors have been discovered, many lack NMDA receptor specificity and are too toxic for clinical studies [Porter, *Epilpsia*, 30 S29–34, 1989]. Thus, the discovery of this invention of certain hydrazones, hydrazines, semicarbazones and thiosemicarbazones derived from pyridyl ketones, as a superior class of anticonvulsant agents in the Applicant's laboratories is significant. The hydrazones, hydrazines, semicarbazones and thiosemicarbazones derived from pyridyl ketones of this invention are potent, orally active, nonneurotoxic EAA antagonists that hold promise for commercial development as nontoxic, clinically useful antiepileptic drugs for the management of epilepsy in humans.

SUMMARY OF THE INVENTION

It is accordingly one object of the present invention to provide novel hydrazones, hydrazines, semicarbazones and thiosemicarbazones derived from pyridyl ketones and their method of preparation.

It is a further object of the present invention to provide anticonvulsant agents which comprise hydrazones, hydrazines, semicarbazones and thiosemicarbazones derived from pyridyl ketones.

A further object of the present invention is to provide a method for the treatment of convulsive disorders by administration of an effective amount of the pyridyl ketone derived hydrazones, hydrazines, semicarbazones and thiosemicarbazones of this invention.

A further object of the present invention is to provide hydrazones, hydrazines, semicarbazones and thiosemicarbazones belonging to three series of pyridyl ketone derivatives and methods for their use in the treatment of neurological disorders such as epilepsy and stroke.

A still further object of the present invention is to provide hydrazones, hydrazines, semicarbazones and thiosemicarbazones derived from pyridyl ketones, as inhibitors of the EAA neurotransmitter L-glutamate. The hydrazones, hydrazines, semicarbazones and thiosemicarbazones derived from pyridyl ketones, of this invention, afford pronounced protection in the maximal electroshock seizure (MES) model in both mice and rats, by the intraperitoneal and oral route, which is indicative of their action as glutamate antagonists.

A still further object of the present invention is to provide anticonvulsant compositions which are highly active by the oral route and contain as the essential ingredient certain hydrazones, hydrazines, semicarbazones and thiosemicarbazones derived from pyridyl ketones, and use of these hydrazones, hydrazines, semicarbazones and thiosemicarbazones derived from pyridyl ketones as potent orally active, nonneurotoxic antiepileptic drugs in the treatment of convulsive disorders such as epilepsy.

Other objects and advantages of the present invention include use of the hydrazones, hydrazines, semicarbazones and thiosemicarbazones derived from pyridyl ketones in the treatment of stroke and other neurological disorders such as Parkinson's disease, by virtue of their action as EAA antagonists and inhibitors of L-glutamate neurotransmission.

In satisfaction of the foregoing objects and advantages, there are provided by this invention hydrazones, hydrazines, semicarbazones and thiosemicarbazones derived from pyridyl ketones which are useful as anticonvulsant drugs. The various groups of pyridyl ketone derived compounds may be characterized by the following general formulae:

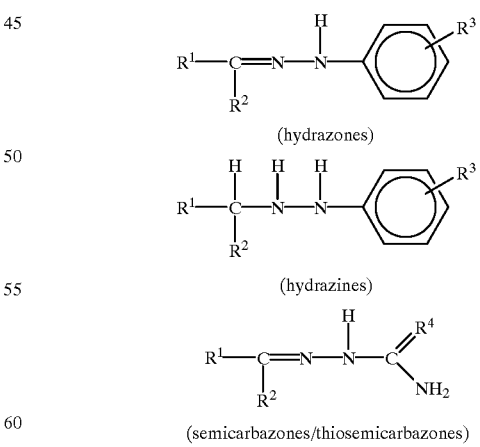

wherein $R^1$ is 2-pyridyl, 3-pyridyl, or 4-pyridyl, $R^2$ is methyl, ethyl or phenyl, $R^3$ is 3,4-dichloro, p or m-chloro, p- or m-bromo, p- or m-fluoro, p- or m-trifluoromethyl, p-lower alkyl, p-lower alkoxy or hydrogen, and $R^4$ is oxygen or sulphur.

Also provided by this invention are orally active, nontoxic anticonvulsant compositions comprising as the active ingredient, a compound selected from those of the following formulae:

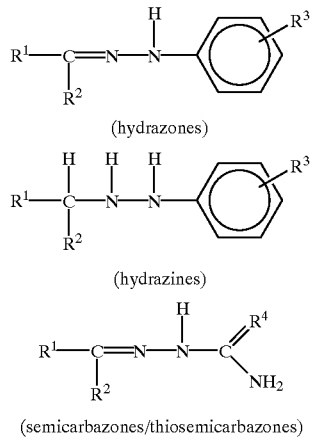

(hydrazones)

(hydrazines)

(semicarbazones/thiosemicarbazones)

wherein $R^1$ is 2-pyridyl, 3-pyridyl or 4-pyridyl, $R^2$ is methyl, ethyl or phenyl, $R^3$ is 3,4-dichloro, p- or m-chloro, p- or m-bromo, p- or m-fluoro, p- or m-trifluoromethyl, p-lower alkyl, p-lower alkoxy or hydrogen, and $R^4$ is oxygen or sulphur.

Also provided are methods for the administration of the anticonvulsant compositions of this invention to mammals including animals and humans in the treatment of convulsive disorders such as epilepsy including partial and generalized seizures.

DESCRIPTION OF PREFERRED EMBODIMENTS

As indicated above, this invention relates to several new compounds belonging to three groups each of hydrazones, hydrazines, semicarbazones and thiosemicarbazones, which are useful as antiepileptic agents. In one group of hydrazones, hydrazines, semicarbazones and thiosemicarbazones, the $R^1$ is 2-pyridyl, in the second group, $R^1$ is 3-pyridyl and in the third group, $R^1$ is 4-pyridyl. In all three groups of hydrazones, hydrazines, semicarbazones and thiosemicarbazones of this invention, the $R^2$ group on the pyridyl ketone carbon is methyl, ethyl or phenyl. The hydrazones and hydrazines of this invention are further substituted on the phenyl group by 3,4-dichloro, p-chloro, or m-chloro, p or m-bromo, p- or m-fluoro, p- or m-trifluoromethyl, plower alkyl, p-lower alkoxy or hydrogen. The hydrazones, hydrazines, semicarbazones and thiosemicarbazones derived from pyridyl ketones of this invention have potent oral anticonvulsant activity as antiepileptic drugs in the treatment of convulsive disorders such as epilepsy including partial seizures and generalized seizures.

In one aspect of the present invention, two groups each of hydrazones, hydrazines, semicarbazones and thiosemicarbazones are provided which have potent oral antiepileptic activity and which are of the following general formulae:

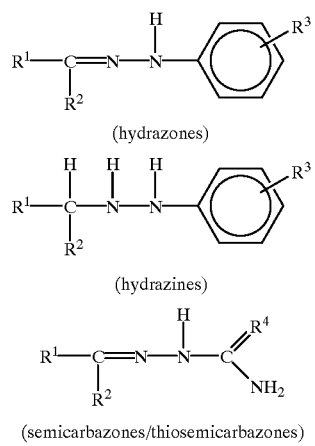

(hydrazones)

(hydrazines)

(semicarbazones/thiosemicarbazones)

In the above formulae, $R^1$ is 3-pyridyl or 4-pyridyl, and R2 is methyl, ethyl or phenyl and leads to the two groups of hydrazones, hydrazines, semicarbazones and thiosemicarbazones. When $R^2$ is methyl, ethyl or phenyl, $R^1$ can be 4-pyridyl or 3-pyridyl and $R^3$ can be 3,4-dichloro, p-chloro or m-chloro. When $R^2$ is methyl, ethyl, or phenyl and $R^1$ is 4-pyridyl or 3-pyridyl, $R^4$ can be oxygen. Those compounds wherein $R^1$ is 4-pyridyl or 3-pyridyl, $R^2$ is methyl, ethyl or phenyl, $R^3$ is 3,4-dichloro, p-chloro, or m-chloro and $R^4$ is oxygen, are new and novel compounds.

In a second aspect of this invention, there are provided novel anticonvulsant compositions which are orally active and nontoxic, and which comprise as the active ingredient an effective amount of a compound selected from those of the following formulae:

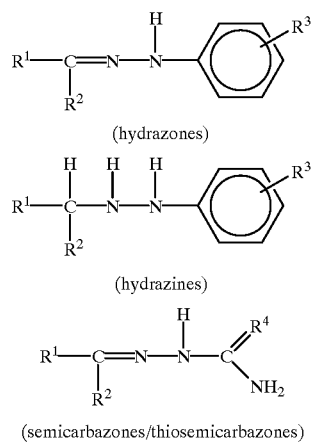

(hydrazones)

(hydrazines)

(semicarbazones/thiosemicarbazones)

wherein $R^1$ is 4-pyridyl or 3-pyridyl, $R^2$ is methyl, ethyl or phenyl, $R^3$ is 3,4-dichloro, p-chloro or m-chloro, and $R^4$ is oxygen.

There are further provided by this invention methods for administration of the anticonvulsant composition to mammals including animals and humans.

In a third aspect of this invention, there are provided hydrazone, hydrazine, and semicarbazone compounds of the formulae:

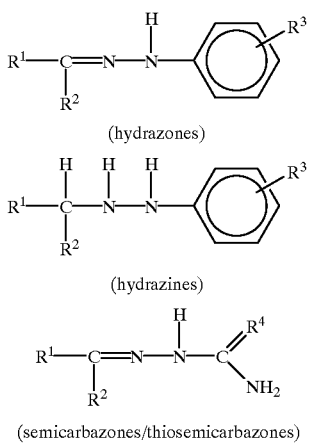

(hydrazones)

(hydrazines)

(semicarbazones/thiosemicarbazones)

wherein $R^1$ is 4-pyridyl or 3-pyridyl, $R^2$ is methyl, ethyl or phenyl, $R^3$ is 3,4-dichloro, p-chloro or m-chloro, and $R^4$ is oxygen and which exhibit pronounced and selective activity in the MES test.

Significance of Pronounced, Selective Activity in the MES Test

The hydrazones, hydrazines, semicarbazones and thiosemicarbazones derived from pyridyl ketones in this invention exhibit pronounced and selective anticonvulsant activity in the maximal electroshock seizure (MES) test but show no activity in the subcutaneous Metrazrole test (scMet). The activity of the compounds of this invention in the MES test is of great significance, because partial seizures in humans correlate positively with experimental seizures elicited by the MES test [Porter, R. J. and Pitlick, W. H., In "Basic and Clinical Pharmacology", 4th Edn., B. G. Katzung Ed., Appleton & Lange, C. A., 1989, pp 287–303]. Since antiepileptic drugs effective against MES seizures alter ionic transport across excitable membranes, the hydrazones, hydrazines, semicarbazones and thiosemicarbazones derived from pyridyl ketones that evince significant activity in the MES test, may be expected to attenuate EAA neurotransmission. Since there is strong evidence that the excitatory neurotransmitter glutamate plays a key role in EAA neurotransmission along limbic circuits which are particularly relevant to kindling epileptogenesis, the pyridyl ketones-derived hydrazones, hydrazines, semicarbazones and thiosemicarbazones of this invention could be expected to be effective glutamate antagonists.

Structural Modifications of the Aminoalkylpyridines at the Amino Group

Studies by the Applicant on the metabolism and pharmacology of triazoline anticonvulsants, led to the evolution and discovery of the aminoalkylpyridines (AAPs) as a unique class of orally active anticonvulsant agents, superior to the triaolines themselves [Kadaba, P. K., et al., Bioorg. Med. Chem., 2, 165–178 (1996); Kadaba, P. K., U.S. Pat. Nos. 4,511,572; 4,618,681; 4,689,334; 4,610,994; 4,820,721]. Work on the aminoalkylpyridines indicate they are nontoxic, and highly effective by the oral route, with protective indices greater than 20. The AAPs also show high anticonvulsant activity in the MES test and are practically inactive in the scMet test (Deshmukh, T. R. & Kadaba, P. K., Med. Chem. Res., 3, 223–232, 1993]. The AAPs are amenable to structural modifications at three sites on the molecule, the pyridyl group, the alkyl group and the amino group. Several structural modifications were effected at the amino site of the AAPs, and from these modifications thereof have evolved the hydrazones, hydrazines, semicarbazones and thiosemicarbazones derived from pyridyl ketones. Several of these derivatives show much greater potency in the MES test and much higher protective index (P.I.) values than the parent AAPs.

NMDA receptor overstimulation by glutamate is implicated in epileptogenesis and epilepsy. Thus, NMDA antagonists also provide prophylaxis and seizure protection. There is a definite need for safer, orally active NMDA antagonists, to afford effective therapies for the epilepsies. Excessive levels of glutamate are suspected not only in epilepsy, but in several other neurological disorders, eg. stroke. Thus, the nontoxic, orally active NMDA antagonists developed from hydrazones, hydrazines, semicarbazones and thiosemicarbazones that are derived from pyridyl ketones in this invention, have good potential for commercial application as clinically useful antiepileptic drugs and also as neuroprotective agents in related neurological disorders such as stroke, Parkinson's disease, etc.

This invention relates to novel, new and previously unknown hydrazones, hydrazines, semicarbazones and thiosemicarbazones derived from pyridyl ketones, as a unique class of potential EAA antagonists, their methods of preparation, and compositions for their use as a novel class of antiepileptic drugs in the treatment of convulsive disorders such as epilepsy including partial and generalized seizures.

Considerable evidence has accrued in the last decade and a half implicating amino acids in chemical neurotransmission; while GABA (gamma-aminobutyric acid) and glycine serve as inhibitory neurotransmitters, L-glutamate and L-aspartate function as excitatory neurotransmitters in the central nervous system [Foster, A. C. and Fagg, G. E., Brain Res. Rev., 7, 103 (1984)]. There exist considerable data that suggest excitatory amino acids (EAAs) may be critically involved in both epileptogenesis and as a focus for the mechanism of action of anticonvulsants (Meldrum, B. S., and Chapman, A. G., In "Glutamine, Glutamate, and GABA in the Central Nervous System," L. Hertz, et al., Ed., Alan R. Liss, Inc., New York 1983, pp. 625–641; R. Schwarcz and Yehezkel-Ben Ari, Eds., "Excitatory Amino Acids and Epilepsy", Plenum Press, New York, 1986). Because brain function in the normal state is a dynamic balance of excitatory and inhibitory processes, one would think that excessive neuronal activity leading to seizures may result from either an increase in excitatory transmission, or alternately, from a decrease in inhibitory transmission. Thus, effecting changes in the concentrations of either excitatory or inhibitory neurotransmitters at their synapses would represent potential mechanisms of anticonvulsant action and strategies for anticonvulsant drug design.

Strong evidence exists for the prominent role of EAAs in excitatory transmission along limbic circuits which are believed to be particularly relevant to kindling epileptogenesis. More recently, evidence for a causal connection between EAA release and onset of hyperactivity has been provided by the use of specific EAA receptor antagonists in various models of epilepsy [Watkins, J. C., and Evans, R. H. Ann. Rev. Pharmacol. Toxicol., 21, 165 (1982)]. There is mounting evidence that the excitatory neurotransmitters, L-glutamate and L-aspartate, play a key role in the spread of epileptic activity from one brain region to another and may also be contributing to its initiation (Meldrum, B. S., In "Handbook of Experimental Pharmacology: Antiepileptic Drugs," H. H. Frey and D. Janz Ed., Berlin, 1984). EAA agonists are convulsants and EAA antagonists show anticonvulsant activity in a variety of seizure models. NMDA receptor overstimulation by high levels of L-glutamate has been implicated in epileptogenesis and epilepsy. NMDA receptor antagonists that block the action of L-glutamate, and thus the overstimulation of the NMDA receptor, may represent novel antiepileptic agents that can afford both prophylaxis as well as seizure protection.

The compounds of the present invention are useful in pharmaceutical compositions using conventional pharmaceutical carriers or vehicles for administration to humans and animals in unit dosage forms, such as tablets, capsules, pills, powders, granules, suppositories, sterile parenteral solutions or suspensions, sterile non-parenteral solutions or suspensions, oral solutions or suspensions, oil in water or water in oil emulsions and the like, containing suitable quantities of the active ingredient.

The hydrazone compounds of this invention may be prepared by reaction of alkyl or aryl pyridyl ketones, when $R^1$ is 3- or 4-pyridyl and $R^2$ is methyl, ethyl or phenyl, with phenylhydrazines when $R^3$ is 3,4-dichloro, p-chloro or m-chloro. The hydrazine compounds are prepared by reduction of the hydrazone compounds with excess borane at room temperature and converting the hydrazine products to the stable hydrochloride salts, as shown in Equation 1.

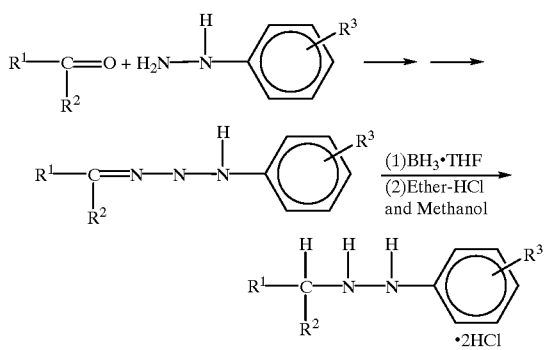

EQUATION 1

In the above equation, $R^1$, $R^2$ and $R^3$ are as defined above.

In the method of preparation, the reaction between the pyridyl ketones and the phenylhydrazine is carried out by condensing the appropriate pyridyl ketone and phenylhydrazine, in an organic solvent such as methanol containing about 4% water. The reaction is conducted at an elevated temperature ranging from about 50° C. to the boiling point of the solvent mixture used optionally under pressure and with agitation. Preferably the reaction is conducted in the absence of the sodium acetate catalyst which is normally employed in this type of condensation reactions. The phenylhydrazine reagent is used in the form of its hydrochloride salt.

After formation of the hydrazones of the pyridyl ketones by this reaction, the reduction to the respective hydrazines is carried out preferably using tetrahydrofuran as the solvent in which the borane reducing agent is present as a borane-tetrahydrofuran complex, indicated by the structure $BH_3$.THF. The reaction is conducted with agitation at room temperature, and the resulting hydrazine compound converted to the stable hydrochloride salt by treatment with an ethereal solution of hydrogen chloride mixed with methanol.

The following examples are presented to illustrate the invention, but it is not to be considered as limited thereto. In the examples and throughout the specification, parts are by weight unless otherwise indicated.

EXAMPLE 1

Preparation of pyridyl ketone hydrazones (hydrazones derived from pyridyl ketones).

To a solution of the appropriate phenylhydrazine hydrochloride (15 mmol) in a mixture of methanol (80 ml) and water (3 ml) was added the pyridyl ketone (15 mmol) and the mixture was refluxed for 5 hours. At the end of the reaction, the mixture was concentrated in vacuo to remove the solvent until a massive precipitate appeared. It was filtered and dissolved in a mixture of ethanol (100 ml) and water (300 ml). The resulting solution was neutralized with sodium bicarbonate whereupon a lot of yellowish precipitate was obtained. The mixture was cooled, the precipitate filtered and crystallized from a methanol (3 parts)-acetone (1 part) mixture to afford the pure pyridyl ketone hydrazones in yields varying from 23% to 87%.

The hydrazones that were prepared according to the above described procedure are all new and are given in Table 1 along with their melting points and yields.

TABLE 1

| | Compound | Melting Point, °C. | Yield, % |
|---|---|---|---|
| (1) | Methyl 4-pyridyl ketone 3,4-dichlorophenylhydrazone | 208.5–210 | 50 |
| (2) | Methyl 4-pyridyl ketone 4-chlorophenylhydrazone | 162–164 | 76 |
| (3) | Methyl 4-pyridyl ketone 3-chlorophenylhydrazone | 170–172 | 77 |
| (4) | Methyl 3-pyridyl ketone 3,4-dichlorophenylhydrazone | 194–196 | 72 |
| (5) | Methyl 3-pyridyl ketone 4-chorophenylhydrazone | 169–172 | 67 |
| (6) | Methyl 3-pyridyl ketone 3-chlorophenylhydrazone | 172–174 | 87 |
| (7) | Ethyl 4-pyridyl ketone 3,4-dichlorophenylhydrazone | 206–210.5 | 34 |
| (8) | Ethyl 4-pyridyl ketone 4-chlorophenylhydrazone | 154–158 | 23 |
| (9) | Ethyl 4-pyridyl ketone 3-chorophenylhydrazone | 182–186 | 25 |
| (10) | Phenyl 4-pyridyl ketone 3,4-dichlorophenylhydrazone | 181–184 | 35 |
| (11) | Phenyl 4-pyridyl ketone 4-chlorophenylhydrazone | 221–223 | 26 |
| (12) | Phenyl 4-pyridyl ketone 3-chorophenylhydrazone | 178–182 | 30 |

EXAMPLE 2

Preparation of 1-(phenyl)-2-[1-(pyridyl)]ethylhydrazine dihydrochlorides.

A solution of the alkyl or aryl pyridyl ketone hydrazone (8.14 mmol) in 1 Molar borane-tetrahydrofuran complex (40 ml–60 ml) (40–60 mmol) was stirred at room temperature for 20–24 hours. The excess borane-tetrahydrofuran complex was removed using a rotary evaporator when a brownish yellow or yellow oily residue was obtained. This was dissolved in methanol (10 ml) and treated with an ethereal solution of hydrogenchloride (1M, Aldrich Chemicals) (20 ml) and stirred at room temperature for 4–6 hours, when a massive white precipitate appeared. It was filtered and crystalized from a mixture of methanol-acetone-ether or methanol-ether.

The hydrazines prepared by the above procedure are all new, and are presented in Table 2, along with their melting points and yields.

TABLE 2

| Compound | Melting Point, °C. | Yield, % |
|---|---|---|
| (1) 1-(4-chlorophenyl)-2-[1-(4-pyridyl)]ethylhydrazine dihydrochloride | 199(d) | 51 |
| (2) 1-(3-chlorophenyl)-2-[1-(4-pyridyl)]ethylhydrazine dihydrochloride | 190(d) | 57 |
| (3) 1-(3,4-Dichlorophenyl)-2-[1-(3-pyridyl)]ethylhydrazine dihydrochloride | 199(d) | 68 |
| (4) 1-(4-Chlorophenyl)-2-[1-(3-pyridyl)]ethylhydrazine dihydrochloride | 195(d) | 46 |
| (5) 1-(3-Chlorophenyl)-2-[1-(3-pyridyl)]ethylhydrazine dihydrochloride | 221(d) | 46 |

The semicarbazones of this invention may be prepared by reaction of alkyl or aryl pyridyl ketones, when $R^1$ is 3- or 4-pyridyl and $R^2$ is methyl, ethyl, or phenyl, with semicarbazide when $R^4$ is oxygen, as shown in Equation 2.

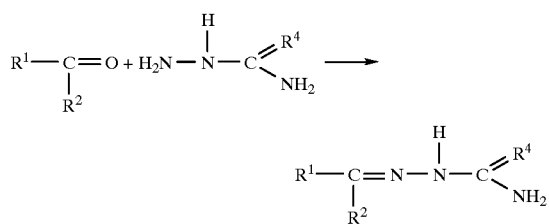

EQUATION 2

In the above equation, $R^1$, $R^2$ and $R^4$ are as defined above.

In the method of preparation, the reaction between the alkyl or aryl pyridyl ketones and the semicarbazide in the form of its hydrochloride salt is carried out by condensing the appropriate pyridyl ketone with the semicarbazide hydrochloride in methanol-water mixture in the presence of fused sodium acetate as a catalyst. The reaction mixture is heated to the boiling point of the solvent mixture and maintained at that temperature for the duration of the reaction.

The following examples are presented to illustrate the invention, but it is not to be considered as limited thereto. In the examples and throughout the specification, parts are by weight unless otherwise indicated.

EXAMPLE 3

Preparation of alkyl or aryl pyridyl ketone semicarbazones.

To a solution of the appropriate ketone (0.04 mol) in methanol (40 ml), was added a solution of semicarbazide hydrochloride (0.04 mol) and fused sodium acetate (0.04 mol), in water (40 ml). The resulting mixture was refluxed with magnetic stirring for 2 hours. At the end of this period it was cooled to room temperature and allowed to stand for about thirty minutes, when a precipitate was obtained. In those cases where no precipitate appeared, the mixture was either cooled in an ice bath or concentrated using a rotary evaporator followed by cooling. The precipitate of the semicarbazone hydrochloride was filtered, washed with methanol, then dissolved in methanol and neutralized with sodium bicarbonate or sodium hydroxide (20% solution). The mixture was cooled and the precipitate of the free semicarbazone was filtered and crystallized from methanol to yield the pure semicarbazones of alkyl or aryl pyridyl ketones.

The semicarbazones prepared according to the above procedure are all new and are given in Table 3 along with their melting points and yields.

TABLE 3

| Compound | Melting Point, °C. | Yield, % |
|---|---|---|
| (1) Methyl 4-pyridyl ketone semicarbazone | 202–204 | 62 |
| (2) Methyl 3-pyridyl ketone semicarbazone | 188–191.5 | 72 |
| (3) Ethyl 4-pyridyl ketone semicarbazone | 194–195.5 | 57 |
| (4) Ethyl 3-pyridyl ketone semicarbazone | 168–172.5 | 86 |
| (5) Phenyl 4-pyridyl ketone semicarbazone | 203–206.5 | 42 |
| (6) Phenyl 3-pyridyl ketone semicarbazone | 165–166.5 | 74 |

All the compounds in Table 1, Table 2 and Table 3 were identified through their elemental analyses, melting points, $^1$H NMR and $^{13}$C NMR spectra.

EXAMPLE 4

The hydrazones, hydrazines and semicarbazones derived from pyridyl ketones and the resulting orally effective anticonvulsant compositions of this invention are useful in the treatment of convulsive disorders. The oral potency of the compounds range from those which are very highly potent to those of good medium potency, with no accompanying toxicity. A series of hydrazones, hydrazines and semicarbazones derived from pyridyl ketones of this invention has been evaluated for anticonvulsant activity by the intraperitoneal (i.p.) and by the oral (p.o.) route using two standard seizure models in the mouse and in the rat, the maximal electroshock seizure (MES) test and the subcutaneous pentylenetetrazole (Metrazole) seizure threshold (scMet) test. These two methods of seizure provocation reliably elicit well characterized seizure phenomena and together they have been shown sufficient to identify all compounds known to demonstrate anticonvulsant activity in other tests [Porter, R. J., et al., *Cleveland Clinic Quarterly*, 51, 293 (1984)]. In addition, the compounds are evaluated in a new model, the threshold tonic extension (TTE) model. The TTE test is similar to the MES test but uses a lower level of electric current, which makes the test more sensitive but less selective than the MES test. Thus active compounds that may be missed in the MES and scMet tests in the mouse, i.p., can be detected in the TTE test.

Based on the screening results, the compounds are placed in one of three categories. Those failing to demonstrate anticonvulsant activity at doses up to 300 mg/kg are considered inactive. Class II compounds show anticonvulsant activity at doses greater than 100 mg/kg or show activity at 100 mg/kg which is not reinforced by similar activity at 300 mg/kg. Thus, compounds of class or group II demonstrate anticonvulsant activity without signs of neurological deficit, but do not have significant potency. The Class I compounds are those which are most promising as anticonvulsants. They demonstrate anticonvulsant activity in either the MES test or the scMet test, or both at doses of 100 mg/kg or 30 mg/kg without signs of neurological deficit and thus have an estimated protective index of greater than 1.

Neurotoxicity is determined by the rotorod ataxia test in mice and by the positional sense test and gait and stance test in the rat.

The following Table 4 presents the results of these anticonvulsant tests with respect to several hydrazone, hydrazine and semicarbazone compounds derived from pyridyl ketones of the present invention. This Table 4 identifies the specific compounds tested by their chemical name and provides the test model, the route of administration, the animal species used, and the anticonvulsant activity based on classification in Group I or Group II, when intraperitoneally administered to mice, and based on percent protection, when orally administered to rats.

As shown in Table 4, all the hydrazones, hydrazines, and semicarbazones derived from pyridyl ketones belong to Class I and demonstrate anticonvulsant activity at doses of 30 mg/kg to 100 mg/kg, without signs of neurological deficit. The anticonvulsant activity of the compounds is far more pronounced in the MES test with hardly any activity in the scMet test, in both mice and rats, by the i.p. and oral routes of administration, respectively, and protective indices greater than 20 and some cases greater than 64 are obtained by oral administration in the rat.

Anticonvulsant quantification in mice, i.p., for five compounds (Table 5) further confirms the greater potency of the hydrazones, hydrazines, and semicarbazones derived from pyridyl ketones in the MES test; in the scMet test, protection is obtained only at high dose levels nearing toxic doses. Anticonvulsant quantification in rats, p.o. (Table 6) clearly shows that the hydrazones, hydrazines, and semicarbazones derived from pyridyl ketones, as a class, are ineffective in the scMet test, but evince a remarkably high degree of anticonvulsant activity by the oral route in the MES seizure model with P.I. values >20 to 64.

The potent activity of the hydrazones, hydrazines and semicarbazones derived from pyridyl ketones, in the MES test is of great significance, because drugs used in the treatment of the two major types of seizures (partial and generalized) are quite distinct in their clinical effects. They also fall into two pharmacological classes, even though seizures may be induced experimentally by a wide variety of methods. The clinical aspects of certain generalized seizures, especially absence seizures, are highly correlated with experimental seizures produced in the scMet model. Likewise, partial seizures in humans correlate positively with experimental seizures elicited by the MES test (Porter, R. J. and Pitlick, W. H., In "Basic and Clinical Pharmacology", 4th Ed., B. G. Katzung Ed., Appleton & Lange, C. A., 1989, pp. 287–303).

TABLE 4

| | Compound | ASP Group Classification, Mouse, i.p. | | Percent Protection* at 30 mg/kg, in the MES test, rat, p.o. |
| --- | --- | --- | --- | --- |
| | | MES Test | TTE Test (Percent Protection)* | |
| (1) | Methyl 4-pyridyl ketone 3,4-dichlorophenylhydrazone | III | I (62%) | 25–95 |
| (2) | Methyl 4-pyridyl ketone 4-chlorophenyl hydrazone | I | — | 50–75 |
| (3) | Methyl 4-pyridyl ketone 3-chlorophenyl hydrazone | II | — | 50–100 |
| (4) | Methyl 3-pyridyl ketone 3,4-dichlorophenylhydrazone | I | — | 25–100 |
| (5) | Methyl 3-pyridyl ketone 4-chlorophenylhydrazone | I | — | 50–100 |
| (6) | Methyl 3-pyridyl ketone 3-chlorophenylhydrazone | I | — | — |
| (7) | Ethyl 4-pyridyl ketone 3,4-dichlorophenylhydrazone | III | I (25%) | — |
| (8) | Ethyl 4-pyridyl ketone 4-chlorophenylhydrazone | I | — | — |
| (9) | Phenyl 4-pyridyl ketone 3,4-dichlorophenylhydrazone | III | I (25 %) | — |
| (10) | Phenyl 4-pyridyl ketone 4-chlorophenylhydrazone | I | — | — |
| (11) | Phenyl 4-pyridyl ketone 3-chlorophenylhydrazone | III | I (25–50%) | — |
| (12) | 1-(3,4-dichlorophenyl)-2-[1-(3-pyridyl)]ethylhydrazine dihydrochloride | I | — | 25–75% |
| (13) | Methyl 4-pyridyl ketone semicarbazone | I | — | — |
| (14) | Methyl 3-pyridyl ketone semicarbazone | II | — | — |
| (15) | Phenyl 4-pyridyl ketone semicarbazone | I | — | 50–100 |
| (16) | Phenyl 3-pyridyl ketone semicarbazone | I | — | 75–100 |

*Percent protection is defined as the ratio between the number of animals protected and the number of animals tested, multiplied by 100, at several time points over a 4-hour period.

TABLE 5

Anticonvulsant Quantification in Mice, i.p.

| Compound | Time of Test (hour)[a] | $ED_{50}$, mg/kg[b,c] | | | $TD_{50}$, mg/kg (rotorod) | P.I., $TD_{50}/ED_{50}$ MES |
| --- | --- | --- | --- | --- | --- | --- |
| | | MES | scMet | TTE | | |
| (1) Methyl 4-pyridyl ketone 3,4-dichlorophenyl hydrazone | —, —, 4, — | — | — | 71.04 (67.04–76.62) [31.25 ± 10.71] | — | — |
| (3) Methyl 4-pyridyl | 2, 2, —, 24 | 81.78 | >500.00 | — | 441.28 | 5.39 |

TABLE 5-continued

Anticonvulsant Quantification in Mice, i.p.

| Compound | Time of Test (hour)[a] | $ED_{50}$, mg/kg[b,c] MES | scMet | TTE | $TD_{50}$, mg/kg (rotorod) | P.I., $TD_{50}/ED_{50}$ MES |
|---|---|---|---|---|---|---|
| ketone 3-chloro-phenylhydrazone | | (69.79–96.62) [9.38 ± 3.28] | | | (296.02–649.89) [3.75 ± 1.08] | |
| (4) Methyl 3-pyridyl ketone 3,4-di-chlorophenyl hydrazone | 6, 6, —, 0 | 69.76 (61.63–80.72) [11.91 ± 3.41] | >500.00 | — | >500.00 | >7.17 |
| (15) Phenyl 4-pyridyl ketone semi-carbazone | 1, 1, —, 1 | 57.49 (38.63–69.76) [8.11 ± 3.42] | >300.00 | — | 160.31 (—)[d] [4.72 ± 2.28] | 2.79 |
| (16) Phenyl 3-pyridyl ketone semi-carbazone | 0.25, —, —, 0.25 | 21.82 (19.08–24.50) [14.97 ± 4.92] | — | — | 84.56 (74.05–98.80) [8.82 ± 2.57] | 3.87 |

[a]Time of test is given in the order for MES, scMet, TTE and toxicity test. For compound 4, time of test for $TD_{50}$ is given as 0, because no toxicity was observed over a 24-hour period even at a dose of 500 mg/kg.
[b]95% confidence interval in ( ).
[c]slope, regression line ± standard error in [ ].
[d]Confidence interval was not determined because of an apparent discrepancy in the toxicity line at 200 mg/kg.

TABLE 6

Anticonvulsant Quantification in Rats, p.o.

| Compound | Time of Test (hour)[a] | $ED_{50}$, mg/kg[b,c] MES | scMet | $TD_{50}$, mg/kg | P.I., $TD_{50}/ED_{50}$ MES |
|---|---|---|---|---|---|
| (1) Methyl 4-pyridyl ketone 3,4-dichlorophenyl hydrazone | 4, 4, 0. | 16.86 (12.96–20.56) [5.59 ± 1.69] | >250.00 | >500.00 | >29.64 |
| (3) Methyl 4-pyridyl ketone 3-chloro-phenylhydrazone | 4, 4, 0. | 36.62 (22.34–59.83) [2.59 ± 0.68] | >250.00 | >500.00 | >13.65 |
| (5) Methyl 3-pyridyl ketone 4-chloro-phenylhydrazone | 2, 2, 0. | 7.79 (5.15–12.39) [3.59 ± 1.28] | >250.00 | >500.00 | >64.12 |

[a]Time of test is given in the order for MES, scMet and toxicity test. Time of test for $TD_{50}$ is given as 0, because no toxicity was observed over a 24-hour period even at a dose of 500 mg/kg.
[b]95% confidence interval in ( ).
[c]slope, regression line ± standard error in [ ].

TABLE 7

Comparison of Anticonvulsant Efficacy ($ED_{50}$, mg/kg) of AAPs and Pyridyl Ketone Hydrazones and Semicarbazones in the MES Test, Rat, p.o.

$$R^1-\underset{R^2}{\underset{|}{\overset{H}{\overset{|}{C}}}}-\overset{H}{\overset{|}{N}}-\underset{}{\bigcirc}-R^3 \qquad R^1-\underset{R^2}{\underset{|}{C}}=N-\overset{H}{\overset{|}{N}}-\underset{}{\bigcirc}-R^3$$

AAP Compounds            Pyridyl ketone hydrazones

| $R^1$ | $R^2$ | $R^3$ | AAP Compounds | Pyridyl ketone hydrazones |
|---|---|---|---|---|
| 4-Pyridyl | $CH^3$ | 3,4-diCl | 29.7 | 16.9 |
| 3-Pyridyl | $CH_3$ | 4-Cl | 0–75% protection at 50 mg/kg | 7.8 |
| 3-Pyridyl | $CH_3$ | 3-Cl | Class II (active at 300 mg/kg) | Class I (active at 100 mg/kg) |
| 4-Pyridyl | Ph | 4-Cl | Class III | Class I |

TABLE 7-continued

Comparison of Anticonvulsant Efficacy (ED$_{50}$, mg/kg) of AAPs and
Pyridyl Ketone Hydrazones and Semicarbazones in the MES Test, Rat, p.o.

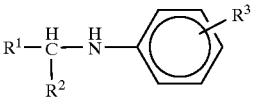

| R$^1$ | R$^2$ | R$^3$ | AAP Compounds | Pyridyl ketone hydrazones |
|---|---|---|---|---|
| | | | | Semicarbazones |
| 4-Pyridyl | Ph | different substituents | generally poor oral activity, 0–50% at 50 mg/kg | 50–100% protection at 30 mg/kg |
| 3-Pyridyl | Ph | different substituents | generally poor oral activity, 0–75% at 50 mg/kg | 75–100% protection at 30 mg/kg |

The anticonvulsant compounds of the present invention may be administered to animals or humans at doses ranging from about 10 mg/kg up to about 200 mg/kg. Preferred levels of administration range from about 10 mg/kg up to 100 mg/kg. The active ingredients or compounds of this invention may be administered in any desired form by injection or in the oral form. Conventional adjuvents and carriers may be employed in combination with about 0.001 to 2.0 wt. % of the active ingredient. Thus, the anticonvulsant compositions of this invention may be administered in pill form or by injection. As indicated above, the dosage rate ranges from about 10 mg/kg up to about 200 mg/kg.

Screening Methodology to Determine Anticonvulsant Activity

In mice. i.p.: All compounds are emulsified in 0.5% methylcellulose. The solvent has been tested for anticonvulsant and toxic effects and found to introduce no significant bias into the testing of anticonvulsant activity. The compounds are administered intraperitoneally in a volume of 0.01 ml/gm to male Carworth Farms #1 mice weighing about 20 gm. All compounds are tested at least at three dose levels (30, 100 and 300 mg/kg) at 30 minutes and 4 hours after their administration.

The Maximal Electroshock Seizure Test (MES): Maximal electroshock seizures are elicited with a 60 Hz alternating current of 50 mA intensity in mice and about 150 mA intensity in rats (5–7 times that necessary to elicit minimal electroshock seizures), delivered for 0.2 sec via corneal electrodes. A drop of 0.9% saline is instilled in the eye prior to application of the electrodes in order to prevent the death of the animal. Abolition of the hind limb tonic extension component of the seizure is defined as protection and results are expressed as number of animals protected/number of animals tested.

The Subcutaneous Pentylenetetrazol (Metrazole) Seizure Treshold Test (scMET): A 0.5 % solution of 85 mg/kg of pentylenetetrazole is administered subcutaneously in the posterior midline 30 minutes or 4 hours after drug administration to the animal. Failure to observe even a threshold seizure (a single episode of clonic spasms of at least 5 sec duration) is defined as protection and the results are expressed as number of animals protected/number of animals tested.

Neurotoxicity is evaluated in mice by the rotorod ataxia test. The animal is placed on a wooden rod of 1 and ⅛" diameter rotating at 6 rpm. Normal mice can remain on a rod rotating at this speed indefinitely. Neurologic toxicity is defined as the failure of the animal to remain on the rod for 1 minute and is expressed as number of animals exhibiting toxicity/number of animals tested.

The Threshold Tonic Extension (TTE) Test: The TTE test (Piredda et al., 1985) is a clinically nonselective, electroconvulsive seizure model that identifies compounds that raise seizure threshold as well as those that prevent seizure spread. In addition, this test can identify certain compounds that are inactive by both the MES and the scMet tests. The test is similar to the MES screen but uses a lower level of electrical current. The lower current makes the TTE test more sensitive but less discriminate than the MES screen. This ability makes the model attractive because it allows us to identify compounds that may be missed by our standard identification screen.

Twenty mice are pretreated intraperitoneally with 100 mg/kg of the test substance. At several time intervals (¼, ½, 1, 2, and 4 hours) post treatment with the test drug, four mice at each time point are challenged with 12.5 mA of electrical current for 0.2 seconds via corneal electrodes. This produces a TTE seizure in the animals (Woodbury and Davenport, 1952).

For each time interval results are expressed as a ratio of the number of animals protected over the number tested. If a compound is found to possess significant activity in the TTE test while remaining inactive in the MES rescreen it becomes a candidate for more advanced testing. The positives may represent compounds acting by novel mechanisms.

Anticonvulsant Quantification in Mice, i.p.: The ED$^{50}$ values are determined in the MES, scMet and rotorod ataxia test. To determine the ED$_{50}$ values, five logarithmically spaced doses of the test compound are administered to animals (male Carworth Farms #1 mice) in groups of eight, to cover 0–100% protection, and the dose required to protect 50% of the animals ($ED_{50}$) together with its 95% confidence limits, is determined graphically.

Anticonvulsant Quantification in Rats p.o.: Substances which exhibit unusual potential as possible antiepileptic drugs, as determined from all prior testing will be subjected to anticonvulsant activity test in the rat (Sprague-Dawley strain). This species will be the subject of the complete anticonvulsant quantification test evaluation as described above, but after oral (gavage) administration of the candidate compound. These results will permit the critical comparison of the anticonvulsant activity and neurotoxicity of the agent under study with similar data previously obtained in mice. Substances which exhibit potential antiepileptic activity will be advanced for toxicity and selected pharmacology studies.

Neurological deficit in rats is examined by the positional sense test and gait and stance test. In the positional sense test, one hind leg is gently lowered over the edge of a table, whereupon the animal will quickly lift it back to normal position. Inability to do so rapidly indicates a neurologic deficit. In the gait and stance test, a neurologic deficit is indicated by a circular or a zigzag gait, ataxia, abnormal spread of the legs, abnormal body posture, tremor, hyperactivity, lack of exploratory behavior, somnolence, stupor, or catalepsy.

Hydrazones, hydrazines and semicarbazones derived from pyridyl ketones as inhibitors of EAA neurotransmission.

EXAMPLE 5

EAAs are known to play important roles in excitatory neurotransmission in partial seizures as discussed earlier. In general, antiepileptic drugs effective against MES seizures alter ionic transport across excitable membranes [Porter, R. J., and Pitlick, W. H., In "Basic and Clinical Pharmacology", 4th Edn., B. G. Katzung, Ed., Appleton and Lange, CA 1989, pp. 287–303]. Based on this rationale, the hydrazones, hydrazines, and semicarbazones derived from pyridyl ketones of this invention which are highly effective in the MES test, can be expected to be effective antagonists of NMDA-receptor mediated EAA neurotransmission and thus can be used to advantage in epilepsy, particularly complex partial seizures, stroke and Parkinson's disease where EAAs play a key role, and where there is a definite need for more effective drugs.

The Therapeutic Potential of Hydrazones, Hydrazines and Semicarbazones Derived from Pyridyl Ketones, as Clinically Useful Antiepileptic Drugs: Potent Orally Active, Nonneurotoxic Anticonvulsant Agents: Our studies on the metabolism and pharmacology of the 1,2,3-triazoline anticonvulsants [P. K. Kadaba, et al., *Bioorg. Med. Chem.* 4, 165–178, (1996)] led to the evolution of the aminoalkylpyridines (AAPs), that show a high degree of anticonvulsant activity by the oral route with no attendant neurotoxicity and with P.I. values >20 [T. R. Deshmukh and P. K. Kadaba, *Med. Chem. Res.*, 3, 223–232 (1993)]. The AAPs are amenable to structural modification at the heterocyclic group, the alkyl moiety and the amino site. Modification of the amino group of several lead AAP compounds by replacing the anilino group by the hydrazono, hydrazino and semicarbazono groups have led to the hydrazones, hydrazines and semicarbazones derived from pyridyl ketones of this invention. Several of these amino group modified AAP compounds, particularly the hydrazones, appear to be superior to the parent AAP anticonvulsant agents (see Table 7 for comparison of activity data).

This invention relating to hydrazones, hydrazines and semicarbazones derived from pyridyl ketones has been described herein with reference to certain preferred embodiments. However, as obvious variations thereon will become apparent to those skilled in the art, the invention is not to be considered as limited thereto.

We claim:

1. A hydrazone compound of the following formulae:

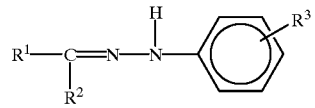

wherein $R^1$ is 4-pyridyl or 3-pyridyl, $R^2$ is methyl, ethyl or phenyl, and $R^3$ is 3,4-dichloro, p-chloro or m-chloro with the proviso that when $R^1$ is 4-pyridyl, and $R^2$ is methyl $R^3$ is not m-chloro and when $R^1$ is 3-pyridyl, and $R^2$ is ethyl $R^3$ is not p-chloro.

2. A hydrazone compound according to claim 1 wherein $R^1$ is 4-pyridyl, $R^2$ is methyl and $R^3$ is 3,4-dichloro.

3. A hydrazone compound according to claim 1 wherein $R^1$ is 4-pyridyl, $R^2$ is methyl and $R^3$ is p-chloro.

4. A hydrazone compound according to claim 1 wherein $R^1$ is 3-pyridyl, $R^2$ is methyl and $R^3$ is 3,4-dichloro.

5. A hydrazone compound according to claim 1 wherein $R^1$ is 3-pyridyl, $R^2$ is methyl and $R^3$ is p-chloro.

6. A hydrazone compound according to claim 1 wherein $R^1$ is 3-pyridyl, $R^2$ is methyl and $R^3$ is m-chloro.

7. A hydrazone compound according to claim 1 wherein $R^1$ is 4-pyridyl, $R^2$ is ethyl and $R^3$ is 3,4-dichloro.

8. A hydrazone compound according to claim 1 wherein $R^1$ is 4-pyridyl, $R^2$ is ethyl and $R^3$ is p-chloro.

9. A hydrazone compound according to claim 1 wherein $R^1$ is 4-pyridyl, $R^2$ is ethyl and $R^3$ is m-chloro.

10. A hydrazone compound according to claim 1 wherein $R^1$ is 4-pyridyl, $R^2$ is phenyl and $R^3$ is 3,4-dichloro.

11. A hydrazone compound according to claim 1 wherein $R^1$ is 4-pyridyl, $R^2$ is phenyl and $R^3$ is p-chloro.

12. A hydrazone compound according to claim 1 wherein $R^1$ is 4-pyridyl, $R^2$ is phenyl and $R^3$ is m-chloro.

13. A hydrazine dihydrochloride compound of the following formulae.

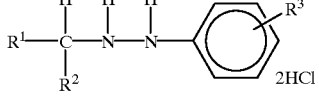

wherein $R^1$ is 4-pyridyl or 3-pyridyl, $R^2$ is methyl and $R^3$ is 3,4-dichloro, p-chloro or m-chloro.

14. A hydrazine dihydrochloride compound according to claim 13 wherein $R^1$ is 4-pyridyl and $R^3$ is p-chloro.

15. A hydrazine dihydrochloride compound according to claim 13 wherein $R^1$ is 4-pyridyl and $R^3$ is m-chloro.

16. A hydrazine dihydrochloride compound according to claim 13 wherein $R^1$ is 3-pyridyl and $R^3$ is 3,4-dichloro.

17. A hydrazine dihydrochloride compound according to claim 13 wherein $R^1$ is 3-pyridyl and $R^3$ is p-chloro.

18. A hydrzine dihydrochloride compound according to claim 13 wherein $R^1$ is 3-pyridyl and $R^3$ is m-chloro.

19. A semicarbazone compound of the following formulae:

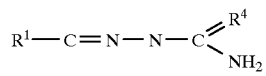

wherein $R^1$ is 4-pyridyl or 3-pyridyl, $R^2$ is methyl, ethyl or phenyl and $R^4$ is oxygen.

20. A semicarbazone compound according to claim 19 wherein $R^1$ is 4-pyridyl and $R^2$ is methyl.

21. A semicarbazone compound according to claim 19 wherein $R^1$ is 3-pyridyl and $R^2$ is methyl.

22. A semicarbazone compound according to claim 19 wherein $R^1$ is 4-pyridyl and $R^2$ is ethyl.

23. A semicarbazone compound according to claim 19 wherein $R^1$ is 3-pyridyl and $R^2$ is ethyl.

24. A semicarbazone compound according to claim 19 wherein $R^1$ is 4-pyridyl and $R^2$ is phenyl.

25. A semicarbazone compound according to claim 19 wherein $R^1$ is 3-pyridyl and $R^2$ is phenyl.

26. A potent orally active, non-neurotoxic anticonvulsant composition, highly effective in the MES or TTE tests and comprising as the active ingredient, an anticonvulsive effective amount of a hydrazone compound selected from the group consisting of those of the formulae:

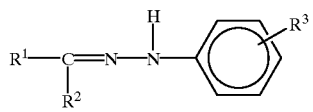

wherein $R^1$ is 4-pyridyl or 3-pyridyl, $R^2$ is methyl, ethyl or phenyl and $R^3$ is 3,4-dichloro, p-chloro or m-chloro, and a pharmaceutical carrier.

27. A composition according to claim 26 wherein $R^1$ is 4-pyridyl, $R^2$ is methyl and $R^3$ is 3,4-dichloro.

28. A composition according to claim 26 wherein $R^1$ is 4-pyridyl, $R^2$ is methyl and $R^3$ is p-chloro.

29. A composition according to claim 26 wherein $R^1$ is 4-pyridyl, $R^2$ is methyl and $R^3$ is m-chloro.

30. A composition according to claim 26 wherein $R^1$ is 3-pyridyl, $R^2$ is methyl and $R^3$ is 3,4-dichloro.

31. A composition according to claim 26 wherein $R^1$ is 3-pyridyl, $R^2$ is methyl and $R^3$ is p-chloro.

32. A composition according to claim 26 wherein $R^1$ is 3-pyridyl, $R^2$ is methyl and $R^3$ is m-chloro.

33. A composition according to claim 26 wherein $R^1$ is 4-pyridyl, $R^2$ is ethyl and $R^3$ is 3,4-chloro.

34. A composition according to claim 26 wherein $R^1$ is 4-pyridyl, $R^2$ is ethyl and $R^3$ is p-chloro.

35. A composition according to claim 26 wherein $R^1$ is 4-pyridyl, $R^2$ is phenyl and $R^3$ is 3,4-dichloro.

36. A composition according to claim 26 wherein $R^1$ is 4-pyridyl, $R^2$ is phenyl and $R^3$ is p-chloro.

37. A composition according to claim 26 wherein $R^1$ is 4-pyridyl, $R^2$ is phenyl and $R^3$ is m-chloro.

38. A potent orally active, nonneurotoxic anticonvulsant composition, highly effective in the MES test and comprising as the active ingredient, an anticonvulsive effective amount of a hydrazine dihydrochloride compound selected from the group consisting of those of the formulae:

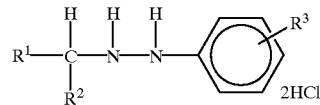

wherein $R^1$ is 4-pyridyl or 3-pyridyl, $R^2$ is methyl, and $R^3$ is 3,4-dichloro, p-chloro or m-chloro, and a pharmaceutical carrier.

39. A composition according to claim 38 wherein $R^1$ is 4-pyridyl and $R^3$ is p-chloro.

40. A composition according to claim 38 wherein $R^1$ is 4-pyridyl and $R^3$ is m-chloro.

41. A composition according to claim 38 wherein $R^1$ is 3-pyridyl and $R^3$ is 3,4-dichloro.

42. A composition according to claim 38 wherein $R^1$ is 3-pyridyl and $R^3$ is p-chloro.

43. A composition according to claim 38 wherein $R^1$ is 3-pyridyl and $R^3$ is m-chloro.

44. A potent orally active, nonneurotoxic anticonvulsant composition, highly effective in the MES test and comprising as the active ingredient, an anticonvulsive effective amount of a semicarbazone compound selected from the group consisting of those of the formulae:

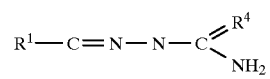

wherein $R^1$ is 4-pyridyl or 3-pyridyl, $R^2$ is methyl, ethyl or phenyl and $R^4$ is oxygen and a pharmaceutical carrier.

45. A composition according to claim 44 wherein $R^1$ is 4-pyridyl and $R^2$ is methyl.

46. A composition according to claim 44 wherein $R^1$ is 3-pyridyl and $R^2$ is methyl.

47. A composition according to claim 44 wherein $R^1$ is 4-pyridyl and $R^2$ is phenyl.

48. A composition according to claim 44 wherein $R^1$ is 3-pyridyl and $R^2$ is phenyl.

49. A composition according to claim 26, claim 38 and claim 44, wherein a sufficient amount of the effective hydrazone, hydrazine or semicarbazone ingredient is contained in said composition to provide a dosage amount ranging from about 10 mg/kg to 200 mg/kg.

50. A method for the treatment of convulsive disorders in mammals which comprises administration thereto of an effective dosage amount of a hydrazone, hydrazine or semicarbazone anticonvulsant composition of claim 26, claim 38 and claim 44.

51. A method according to claim 50 wherein the composition is administered in a dosage amount ranging from about 10 mg/kg to 200 mg/kg of body weight.

* * * * *